United States Patent [19]
Rodgers et al.

[11] Patent Number: 6,096,709
[45] Date of Patent: *Aug. 1, 2000

[54] USE OF ANGIOTENSIN II FRAGMENTS AND ANALOGS THEREOF IN TISSUE REPAIR

[75] Inventors: Kathleen Elizabeth Rodgers, Long Beach; Gere Stodder Dizerega, Pasadena, both of Calif.

[73] Assignee: University of Southern California, Los Angeles, Calif.

[*] Notice: This patent is subject to a terminal disclaimer.

[21] Appl. No.: 09/208,337

[22] Filed: Dec. 9, 1998

Related U.S. Application Data

[63] Continuation of application No. 08/465,775, Jun. 6, 1995, Pat. No. 5,955,430, which is a continuation-in-part of application No. 08/337,781, Nov. 14, 1994, Pat. No. 5,629,292, which is a continuation-in-part of application No. 08/126,368, Sep. 24, 1993, abandoned.

[51] Int. Cl.[7] .......................... A61K 38/06; A61K 38/07; A61K 38/08
[52] U.S. Cl. .................. 514/16; 514/17; 514/18
[58] Field of Search ............................. 514/2, 8, 12, 13, 514/14, 15, 16, 17, 18; 530/316, 324, 325, 326, 327, 328, 329, 330, 331

[56] References Cited

U.S. PATENT DOCUMENTS

| | | | |
|---|---|---|---|
| 4,959,353 | 9/1990 | Brown et al. ............................. 514/12 |
| 5,015,629 | 5/1991 | di Zerega ................................. 514/16 |
| 5,334,532 | 8/1994 | Tackney et al. ..................... 435/252.33 |
| 5,393,740 | 2/1995 | Amagaya et al. ........................ 514/17 |
| 5,436,228 | 7/1995 | Postlethwaite et al. ................. 514/12 |
| 5,457,093 | 10/1995 | Cini et al. ................................ 514/12 |
| 5,591,709 | 1/1997 | Lindenbaum ............................. 514/4 |
| 5,629,292 | 5/1997 | Rodgers et al. ......................... 514/16 |
| 5,658,883 | 8/1997 | Ogawa et al. ............................ 514/12 |
| 5,716,935 | 2/1998 | Rodgers et al. ......................... 514/16 |
| 5,834,432 | 11/1998 | Rodgers et al. ......................... 514/16 |
| 5,955,430 | 9/1999 | Rodgers et al. ......................... 514/16 |

OTHER PUBLICATIONS

Darnell et al. Molecular Cell Biology—New York: Scientific American Books, p. 59, 1986.

H. Gregory. Isolation and Structure of Urogastrone . . . Nature. vol. 257, pp. 325–327, Sep. 25, 1975.

*Primary Examiner*—Jeffrey E. Russell
*Attorney, Agent, or Firm*—Knobbe, Martens, Olson & Bear, LLP

[57] ABSTRACT

Angiotensin II fragments and analogs thereof are useful in accelerating wound healing. These compounds form the basis of compositions useful for accelerating wound healing, in which the active agent is present in an amount effective to accelerate wound healing. Preferably, the compositions are in the form of matrical or micellar solutions.

21 Claims, 14 Drawing Sheets

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: Peptide (xi) SEQUENCE DESCRIPTION: SEQ ID NO:1:

Asp Arg Val Tyr Ile His Pro Phe
 1               5

(2) INFORMATION FOR SEQ ID NO:2:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:2:

Arg Val Tyr Ile His Pro Phe
 1               5

(2) INFORMATION FOR SEQ ID NO:3:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:3:

Val Tyr Ile His Pro Phe
 1               5

(2) INFORMATION FOR SEQ ID NO:4:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:4:

Asp Arg Val Tyr Ile His Pro
 1               5

(2) INFORMATION FOR SEQ ID NO:5:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:5:

Arg Val Tyr Ile His Pro
 1               5

(2) INFORMATION FOR SEQ ID NO:6:

(i) SEQUENCE CHARACTERISTICS:
            (A) LENGTH: 5 amino acids
            (B) TYPE: amino acid
            (C) STRANDEDNESS: single
            (D) TOPOLOGY: linear

```
        (ii) MOLECULE TYPE: Peptide (xi) SEQUENCE DESCRIPTION: SEQ ID NO:6:

Val Tyr Ile His Pro
1               5

(2) INFORMATION FOR SEQ ID NO:7:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:7:

Ile His Pro Phe
1

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:8:

Asp Arg Val Tyr Ile His
1               5

(2) INFORMATION FOR SEQ ID NO:9:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:9:

Asp Arg Val Tyr Ile
1               5

(2) INFORMATION FOR SEQ ID NO:10:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: Peptide (xi) SEQUENCE DESCRIPTION: SEQ ID NO:10:

Asp Arg Val Tyr
1

(2) INFORMATION FOR SEQ ID NO:11:

(i) SEQUENCE CHARACTERISTICS:
            (A) LENGTH: 3 amino acids
            (B) TYPE: amino acid
            (C) STRANDEDNESS: single
```

(D) TOPOLOGY: linear (ii) MOLECULE TYPE: Peptide (xi) SEQUENCE DESCRIPTION: SEQ ID NO:11:

Asp Arg Val
1

(2) INFORMATION FOR SEQ ID NO:12:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO:12:

His Pro Phe
1

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO:13:

Tyr Ile His Pro Phe
1               5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (ix) FEATURE:
        (A) NAME/KEY: Other
        (B) LOCATION: 1...1
        (D) OTHER INFORMATION: Xaa1 is H, Arg, Lys, Ala, Orn, Ser(Ac),
            Sar, D-Arg or D-Lys
        (A) NAME/KEY: Other
        (B) LOCATION: 2...2
        (D) OTHER INFORMATION: Xaa2 is Val, Ala, Leu, Ile, Gly, Pro,
            Aib, Acpc or Tyr
        (A) NAME/KEY: Other
        (B) LOCATION: 4...4
        (D) OTHER INFORMATION: Xaa4 is Ile, Ala, Leu, Val or Gly (xi) SEQUENCE DESCRIPTION: SEQ ID NO:14:

Xaa Xaa Tyr Xaa His Pro Phe
1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear -continued

```
    (ii) MOLECULE TYPE: Peptide (ix) FEATURE:
          (A) NAME/KEY: Other
          (B) LOCATION: 1...1
          (D) OTHER INFORMATION: Xaa1 is Asp, Glu, Asn, Acpc, Ala,
              Me2Gly, Pro, Bet, Glu(NH2), Gly, Asp(NH2) or Suc
          (A) NAME/KEY: Other
          (B) LOCATION: 2...2
          (D) OTHER INFORMATION: Xaa2 is Arg, Lys, Ala, Orn, Ser(Ac),
              Sar, D-Arg, D-Lys
          (A) NAME/KEY: Other
          (B) LOCATION: 3...3
          (D) OTHER INFORMATION: Xaa3 is Val, Ala, Leu, Ile, Gly, Pro,
              Aib, Acpc or Tyr
          (A) NAME/KEY: Other
          (B) LOCATION: 4...4
          (D) OTHER INFORMATION: Xaa4 is Tyr, Thr, Ser or azaTyr
          (A) NAME/KEY: Other
          (B) LOCATION: 5...5
          (D) OTHER INFORMATION: Xaa5 is Ile, Ala, Leu, Val or Gly
          (A) NAME/KEY: Other
          (B) LOCATION: 6...6
          (D) OTHER INFORMATION: Xaa6 is His or Arg
          (A) NAME/KEY: Other
          (B) LOCATION: 7...7
          (D) OTHER INFORMATION: Xaa7 is Pro or Ala
          (A) NAME/KEY: Other
          (B) LOCATION: 8...8
          (D) OTHER INFORMATION: Xaa8 is Phe, Phe(Br), Ile or Tyr (xi) SEQUENCE DESCRIPTION: SEQ ID NO:15:

Xaa Xaa Xaa Xaa Xaa Xaa Xaa Xaa
 1               5
```

USE OF ANGIOTENSIN II FRAGMENTS AND ANALOGS THEREOF IN TISSUE REPAIR

RELATED APPLICATIONS

This application is a continuation of Ser. No. 08/465,775, filed Jun. 6, 1995, now U.S. Pat. No. 5,955,430, which is a continuation-in-part of Ser. No. 08/337,781 filed Nov. 14, 1994, now U.S. Pat. No. 5,629,292, which in turn is a continuation-in-part of Ser. No. 08/126,368 filed Sep. 24, 1993, now abandoned.

FIELD OF THE INVENTION

This invention relates generally to the fields of biochemistry and medicine. More particularly, the present invention relates to compositions and methods for use in accelerating the growth or healing of tissue.

BACKGROUND OF THE INVENTION

Wounds (i.e., lacerations or openings) in mammalian tissue result in tissue disruption and coagulation of the microvasculature at the wound face. Repair of such tissue represents an orderly, controlled cellular response to injury. All soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in great detail and have in some instances been quantified [Hunt, T. K. et al., "Coagulation and macrophage stimulation of angiogenesis and wound healing," in *The surgical wound*, pp. 1–18, ed. F. Dineen & G. Hildrick-Smith (Lea & Febiger, Philadelphia: 1981)].

The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents are in general unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of angiotensin II to wound tissue significantly increases the rate of wound healing, leading to a more rapid re-epithelialization and tissue repair. The term angiotensin II refers to an octapeptide present in humans and other species having the sequence Asp—Arg—Val—Tyr—Ile—His—Pro—Phe [SEQ ID NO:1]. Angiotensin II is a known pressor agent and is commercially available.

Despite the utility of angiotensin II in accelerating wound healing, there remains a need for additional agents which are useful in promoting wound healing. Moreover, it would be highly advantageous to employ an agent which is less potent than angiotensin II at inducing hypertension.

It is an object of the present invention to provide compositions and methods which do not suffer from the drawbacks of the heretofore-known compositions.

SUMMARY OF THE INVENTION

The present invention relates to the use of active fragments of AII and analogs thereof in wound healing. These compounds form the basis of compositions useful for accelerating wound healing, the compositions comprising at least one such compound in an amount effective to accelerate wound healing. Preferably, the compositions are in the form of matrical or micellar solutions.

BRIEF DESCRIPTION OF THE DRAWINGS

The invention may be better understood with reference to the accompanying drawings, in which.

DETAILED DESCRIPTION OF THE INVENTION

Figure 1:
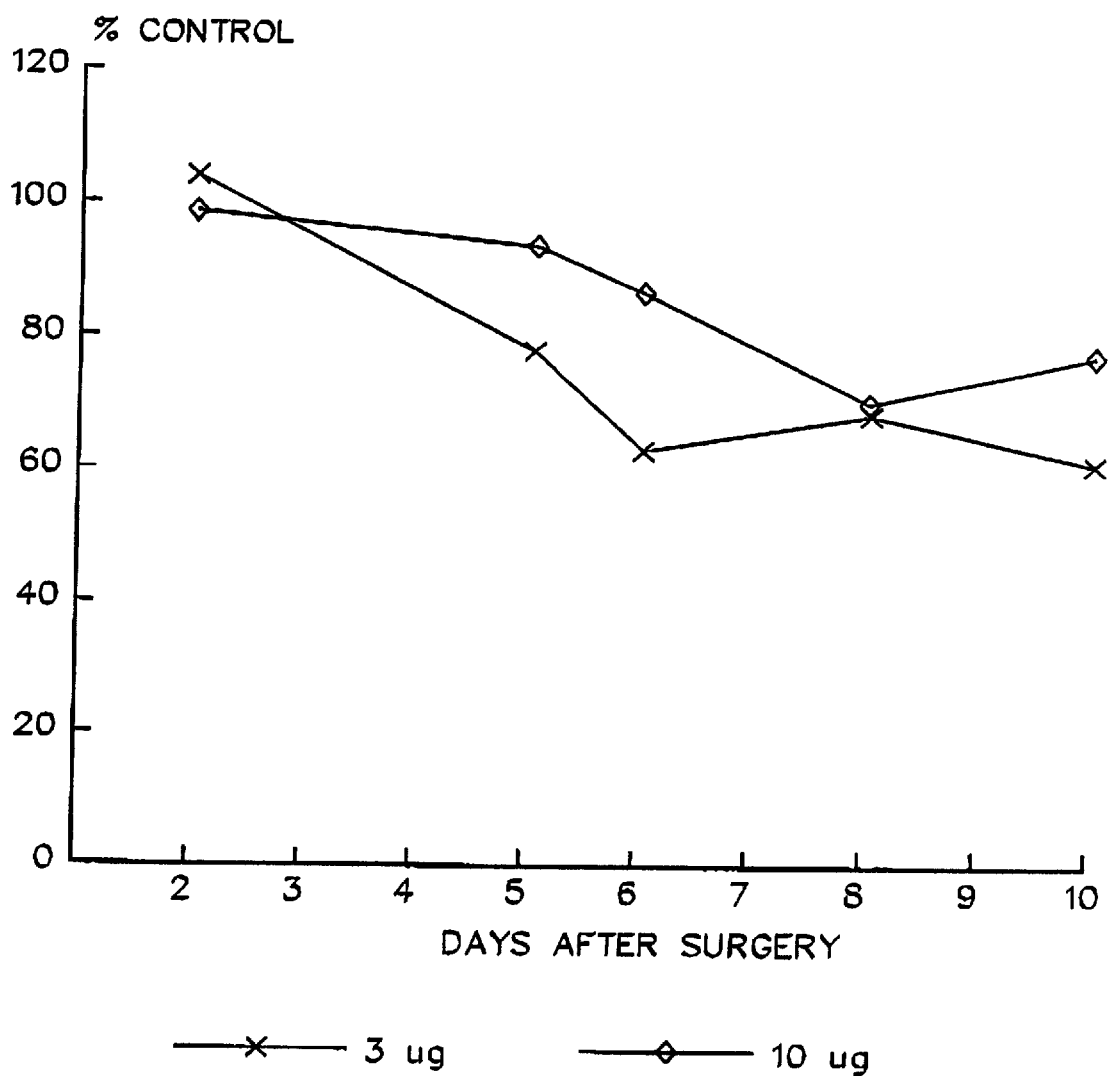
FIG. 1 illustrates the percent increase in wound closure relative to a vehicle-treated control using AIII.

Pursuant to the present invention, wound healing in mammalian tissue is promoted through the use of a composition comprising an effective amount of at least one active fragment of AII or analog thereof. The active agent is generally administered in a matrical or micellar solution and is effective in accelerating re-epithelialization and tissue repair even in very low concentrations.

The active fragments of AII and analogs thereof of particular interest in accordance with the present invention are characterized as comprising a sequence consisting of at least three, and preferably at least four, contiguous amino acids corresponding to a subsequence of groups $R^1$–$R^8$ in the sequence of general formula I

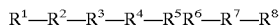

in which $R^1$ and $R^2$ together form a group of formula

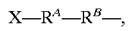

wherein X is H or a one to three peptide group and a peptide bond between $R^A$ and $R^B$ is labile to aminopeptidase A cleavage;

$R^3$ is selected from the group consisting of Val, Ala, Leu, Ile, Gly, Pro, Aib, Acpc and Tyr;

$R^4$ is selected from the group consisting of Tyr, Thr, Ser and azaTyr;

$R^5$ is selected from the group consisting of Ile, Ala, Leu, Val and Gly;

$R^6$ is His or Arg;

$R^7$ is Pro or Ala; and $R^8$ is selected from the group consisting of Phe, Phe (Br), Ile and Tyr, excluding sequences including $R^4$ as a terminal Tyr group.

In one class of preferred embodiments, $R^A$ is suitably selected from Asp, Glu, Asn, Acpc (1-aminocyclopentane carboxylic acid), Ala, Me²Gly, Pro, Bet, Glu(NH₂), Gly, Asp(NH₂) and Suc. $R^B$ is suitably selected from Arg, Lys, Ala, Orn, Ser(Ac), Sar, D-Arg and D-Lys. Particularly preferred combinations for $R^A$ and $R^B$ are Asp—Arg, Asp—Lys, Glu—Arg and Glu—Lys.

Particularly preferred embodiments of this class include the following: AIII or AII(2–8), Arg—Val—Tyr—Ile—His—Pro—Phe [SEQ ID NO:2]; AII(3-8), also known as des1-AIII or AIV, Val—Tyr—Ile—His—Pro—Phe [SEQ ID NO:3]; AII(1–7), Asp—Arg—Val—Tyr—Ile—His—Pro [SEQ ID NO:4]; AII(2–7), Arg—Val—Tyr—Ile—His—Pro [SEQ ID NO:5]; AII(3–7), Val—Tyr—Ile—His—Pro [SEQ ID NO:6]; AII(5–8), Ile—His—Pro—Phe [SEQ ID NO:7]; AII(1–6), Asp—Arg—Val—Tyr—Ile—His [SEQ ID NO:8]; AII(1–5), Asp—Arg—Val—Tyr—Ile [SEQ ID NO:9]; AII (1–4), Asp—Arg—Val—Tyr [SEQ ID NO:10]; and AII (1–3), Asp—Arg—Val [SEQ ID NO:11]. AII(6–8), His—Pro—Phe [SEQ ID NO:12] and AII(4–8), Tyr—Ile—His—Pro—Phe [SEQ ID NO:13] were also tested and found not to be effective.

Another class of compounds of particular interest in accordance with the present invention are those of the general formula II

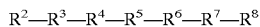

in which $R^2$ is selected from the group consisting of H, Arg, Lys, Ala, Orn, Ser(Ac), Sar, D-Arg and D-Lys;

$R^3$ is selected from the group consisting of Val, Ala, Leu, Ile, Gly, Pro, Aib, Acpc and Tyr;

$R^4$ is selected from the group consisting of Tyr, Thr, Ser and azaTyr;

$R^5$ is selected from the group consisting of Ile, Ala, Leu, Val and Gly;

$R^6$ is His or Arg;

$R^7$ is Pro or Ala; and $R^8$ is selected from the group consisting of Ile, Phe, Phe(Br) and Tyr.

A particularly preferred subclass of the compounds of general formula II has the formula $R^2$—$R^3$—Tyr—$R^5$—His—Pro—Phe [SEQ ID NO:14]

wherein $R^2$, $R^3$ and $R^5$ are as previously defined. Particularly preferred is angiotensin III of the formula Arg—Val—Tyr—Ile—His—Pro—Phe [SEQ ID NO:2]. The fragment AII(4–8) was ineffective in repeated tests; this is believed to be due to the exposed tyrosine on the N terminus.

In the above formulas, the standard three-letter abbreviations for amino acid residues are employed. In the absence of an indication to the contrary, the L-form of the amino acid is intended. Other residues are abbreviated as follows:

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AIII and its analogs adopt either a gamma or a beta turn [Regoli, D. et al. (1974) Pharmacology of Angiotensin. Pharmacological Reviews 26:69]. In general, it is believed that neutral side chains in positions $R^3$, $R^5$ and $R^7$ may be involved in maintaining the appropriate distance between the active groups in positions $R^4$, $R^6$ and $R^8$ primarily responsible for binding to receptors and/or intrinsic activity. Hydrophobic side chains in positions $R^3$, $R^5$ and $R^8$ may also play an important role on the whole conformation of the peptide and/or contribute to formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or non-linear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Ser and azaTyr. In this position, Tyr is particularly preferred as it may form a hydrogen bond with the receptor site capable of accepting a hydrogen from the phenolic hydroxyl [Regoli et al. (1974), supra].

In position $R^5$, an amino acid with a β aliphatic or alicyclic chain is particularly desirable. Therefore, while Gly is suitable in position $R^5$, it is preferred that the amino acid in this position be selected from Ile, Ala, Leu and Val.

In the analogs of particular interest in accordance with the present invention, $R^6$ is His or Arg. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogs of interest to receptors; therefore, Tyr and especially Phe are preferred for purposes of the present invention.

Angiotensin II is one of the most potent vasoconstrictors known, causing constriction of the small arteries that branch to form the capillaries, i.e., the arterioles. The biological formation of angiotensin is initiated by the action of renin on the plasma substrate angiotensinogen. The substance so formed is a decapeptide called angiotensin I which is converted to angiotensin II by the converting enzyme angiotensinase that removes the C-terminal His-Leu residues from angiotensin I.

Studies have shown that the vasoactive product of the renin-angiotensin system, angiotensin II (AII), increases the release of growth factors, mitogenesis, chemotaxis and the release of extracellular matrices of cultured cells that are involved in wound repair [Dzau V. E. et al. (1989) Molecular mechanism of angiotensin in the regulation of vascular and cardiac growth. J Mol Cell Cardiol 21 (Supple III):S7; Berk, B C et al. (1989) Angiotensin II stimulated protein synthesis in cultured vascular smooth muscle cells. Hypertension 13:305–14; Kawahara, Y, et al. (1988) Angiotensin II induces expression of the c-fos gene through protein kinase C activation and calcium ion mobilization in cultured vascular smooth muscle cells. BBRC 150:52–9; Naftilan, A J et al. (1989) Induction of platelet-derived growth factor A-chain and c-myc gene expressions by angiotensin II in cultured rat vascular smooth muscle cells. J Clin Invest 83:1419–24; Taubman, M B et al. (1989) Angiotensin II induces c-fos mRNA in aortic smooth muscle. Role of $Ca^{2+}$ mobilization and protein kinase C activation. J Biol Chem 264:526–530; Nakahara, K et al. (1992) Identification of three types of PDGF-A chain gene transcripts in rabbit vascular smooth muscle and their regulated expression during development and by angiotensin II. BBRC 184:811–8; Stouffer G A and G K Owens. (1992) Angiotensin II induced mitogenesis of spontaneously hypertensive rat derived cultured smooth muscle cells is dependent on autocrine production of transforming growth factor-β. Circ Res 70:820; Wolf, G et al. (1992) Angiotensin II stimulates the proliferation and biosynthesis of type I collagen in cultured murine mesangial cells. Am J Pathol 140:95–107; Bell, L and J A Madri (1990) Influence of the angiotensin system on endothelial and smooth muscle cell migration. Am J Pathol 137:7–12]. In addition, AII was shown to be angiogenic in rabbit corneal eye and chick chorioallantoic membrane models (Fernandez, L A et al. (1985) Neovascularization produced by angiotensin II. J Lab Clin Med 105:141; LeNoble, F A C et al. (1991) Angiotensin II stimulates angiogenesis in the chorio-allantoic membrane of the chick embryo. Eur J Pharmacol 195:305–6]. Therefore, AII may accelerate wound repair through increased neovascularization, growth factor release, reepithelialization and production of extracellular matrix. Through an increase in the flow of blood and nutrients to an injured tissue, AII may increase the rate of wound repair. AII may also accelerate wound repair through the generation of growth factors at the site of injury. Exogenous addition of growth factors has been shown to accelerate wound repair through a variety of mechanisms [Grotendorst, G R et al. (1985) Stimulation of granulation tissue formation by platelet-derived growth factor in normal and diabetic rats. J Clin Invest 76:2323–9; Mustoe, T A et al. (1987) Accelerated healing of incisional wounds in rats induced by transforming growth factor-β. Science 237:1333–5; Pierce, G F et al. (1988) In vivo incisional wound healing augmented by platelet-derived growth factor and recombinant c-sis gene homodimeric proteins. J Exp Med 167:974–87; Lynch, S E et al. (1989) Growth factors in wound healing. J Clin Invest 84:640–6; Greenhalgh, D G et al. (1990) PDGF and FGF stimulate wound healing in the genetically diabetic mouse. Am J Pathol 136:1235–46]. Recent studies showed that AII increased neointima formation in the carotid artery and aorta after injury [Powell, J S et al. (1989) Inhibitors of angiotensin-converting enzyme prevent myointimal proliferation after vascular injury. Science 245:186–8; Powell, J S et al. (1991) The proliferative response to vascular injury is suppressed by converting enzyme inhibition. J Cardiovasc Pharmacol 16 (suppl 4):S42–9; Capron, L et al. (1991) Effect of ramipril, an inhibitor of angiotensin converting enzyme, on the response of rat thoracic aorta to injury with a balloon catheter. J Cardiovasc Pharmacol 18:207–11; Osterriedes, W et al. (1991) Role of angiotensin II injury-induced neointima formation in rats. Hypertension 18:Suppl II60–64; Daemen, MJAP et al. (1991) Angiotensin II induces smooth muscle cell proliferation in the normal and injured rat arterial wall. Circ Res 68:450–6]. As a result of these observations, studies were conducted to determine the mechanism by which endogenous AII may induce intimal hyperplasia. AII was shown to act as a mitogen for smooth muscle cells, fibroblasts and endothelial cells [Schelling, P et al. (1979) Effects of angiotensin II and angiotensin II antagonist saralysin on cell growth and renin in 3T3 and SV3T3 cells. J Cell Physiol 98:503–13; Campbell-Boswell, M and A L Robertson. (1981) Effects of angiotensin II and vasopressin on human smooth muscle cells in vitro. Exp Mol Pathol 35:265–76; Emmett, N et al. (1986) Effect of saralasin (angiotensin II antagonist) on 3T3 cell growth and proliferation. J Cell Biol 103:171 (Abst); Paquet, J L et al. (1990) Angiotensin II-induced proliferation of aortic myocytes in spontaneously hypertensive rats. J Hypertens 8:565–72; Dzau et al, supra]. AII also increased the protein content and size of vascular smooth muscle cells [Berk et al. (1989), supra; Geisterfer, A A T et al. (1988) Angiotensin II induces hypertrophy, not hyperplasia, of cultured rat aortic smooth muscle cells. Circ Res 62:749–56]. Studies showed that AII increases the release of growth factors of various types, including PDGF, heparin-binding EGF and transforming growth factor-β (TGFβ), and growth-related proto-oncogenes from smooth muscle cells, endothelial cells and cardiac fibroblasts [Kawahara et al. (1988), supra; Naftilan, A J (1992) The role of angiotensin II in vascular smooth muscle cell growth. J Cardiovas Pharmacol 20:S37–40; Naftilan et al. (1989), supra; Taubman et al. (1989), supra; Nakahara et al. (1992), supra; Temizer et al (1992), supra; Gibbons, G H et al. (1992) Vascular smooth muscle cell hypertrophy vs hyperplasia. Autocrine transforming growth factor-beta 1 expression determines growth response to angiotensin II. J Clin Invest 90:456–61; Bell, L et al. (1992) Autocrine angiotensin system regulation of bovine aortic endothelial cell migration and plasminogen activator involves modulation of proto-oncogene pp6Oc-src expression. J Clin Invest 89:315–20; Stouffer and Owens (1992), supra]. The hypertrophy of vascular smooth muscle cells by AII was mediated through PDGF [Berk, B C and G N Rao. (1993) Angiotensin II-induced vascular smooth muscle cell hypertrophy: PDGF A-chain mediates the increase in size. J Cell Physiol 154:368–80].

Therefore, it is conceivable that AII acts to accelerate wound repair through increasing the levels of these growth factors in the wound tissue. Additionally, AII was shown to stimulate collagen synthesis thereby suggesting a role for this factor in extracellular matrix formation [Wolf, G et al. (1991) Intracellular signalling of transcription and secretion of type IV collagen after angiotensin II-induced cellular hypertrophy in cultured proximal tubular cells. Cell Reg 2:219–27; Wolf et al. (1992), supra; Zhou, G et al. (1992) Angiotensin II mediated stimulation of collagen synthesis in cultured cardiac fibroblasts. FASEB J 6:A1914]. Wound repair also involves chemotaxis of the necessary cell types into the wound bed. AII was also shown to induce the migration of endothelial cells and smooth muscle cells in vitro [Bell and Madri (1990), supra].

Recent studies also indicate that expression of AII receptors is altered during the process of wound repair [Viswanathan, M, and J M Saavedra (1992) Expression of Angiotensin II $AT_2$ Receptors in the Rat Skin During Experimental Wound Healing. Peptides 13:783–6; Kimura, B et al. (1992) Changes in skin angiotensin II receptors in rats during wound healing. BBRC 187:1083–1090]. These changes, along with evidence of an increase in the local production of AII at the site of repair, suggests that AII may play a key role in the process of wound repair.

It has been observed that AII and AIII have quite different biological activities in several respects. For example, AII showed a biphasic effect on evoked neuronal norepinephrine release (an earlier decrease followed by a later increase), while increasing spontaneous norepinephrine release only after 12 minutes; AIII showed a biphasic effect on both evoked and spontaneous neuronal norepinephrine release [Vatta, M S et al. (1992) Monophasic and biphasic effects of angiotensin II and III on norepinephrine uptake and release in rat adrenal medulla. Can. J. Physiol. Pharmacol. 70:821]. Moreover, AII and AIII show differential influences on the baroreceptor-heart-reflex: AII enhances the sensitivity of the reflex, whereas AIII impairs it [Brattstrom, A. et al. (1992) Neuropeptides within the nucleus tractus solitarii modulate the central cardiovascular control process. Progress in Brain Research 91:75]. Surprisingly, notwithstanding these significant differences in biological activity between angiotensin II and angiotensin III, AIII and particular analogs thereof are useful in accelerating wound healing.

Many studies have focused on AII(1–7) to evaluate its activity. Many of the effects of AII(1–7) are attributed to acting through the AT2 receptor. However, this is not consistent and depends upon the tissue examined.

AII(1–7) does not have many of the effects of AII. AII(1–7) lacks pressor activity or has very mild (effective at 10000–100000 times the dose of AII) effects on blood pressure depending upon the model tested and route of administration. In fact, AII(1–7) has a depressor effect on blood pressure that may be mediated through prostanoid synthesis. In addition, in contrast to the effects of AII, AII(1–7) does not cause catecholamine release and aldosterone release and is not dipsogenic [Webb et al. 1992. Molecular characterization of angiotensin II type II receptors in rat pheochromocytoma cells. Peptides 13:499–508; Cheng et al. 1994. Comparison of pressor responses to angiotensin I, II and III in pulmonary vascular bed of cats. Am. J Physiol 266:H2247–H2255; Moriguchi, A et al. 1994. Differential regulation of central vasopressin in transgenic rats harboring the mouse Ren-2 gene. Am J Physiol 267:R786–R791; Schiavone et al. 1990. Angiotensin-[1–7]: Evidence for novel actions in the brain. J Cardiovascular Pharinacol 16(Suppl 4):S19–S24; Ferrario et al. 1991. Angiotensin-(1–7): A new hormone of the angiotensin system. Hypertension 19[suppl III]:III-126-III-133].

In one report, AII(1–7) is a weak pressor that requires about 10000× more AII(1–7) than AII to get a comparable response [Benter et al. 1993. Cardiovascular actions of angiotensin(1–7). Peptides 14:679–684]. In this system, AII(1–7) had a long depressor effect that was dose dependent. AII(3–7) had less of a pressor effect than AII(1–7), but had no depressor effect. It is also noted that AII(1–7), AII(2–7) and AII(3–7) may affect the dopamine system and memory (suggesting a psychoactive effect).

In several systems, the actions of AII(1–7) are quite distinct from AII. AII stimulates choline production in rat mesangial cells through the AT1 receptor; AII(1–7) and AII(1–6) has very weak effects on this parameter [Pfeilschifter et al. 1992. Angiotensin II stimulation of phospholipase D in rat renal mesangial cells is mediated by the AT1 receptor subtype. Eur J Pharmacol 225:57–62].

In porcine aortic endothelial cells, AI and AII(1–7) stimulated the release of prostaglandin E2 and I2, but AII did not have this effect [Jaiswal et al. 1992. Stimulation of endothelial cell prostaglandin production by angiotensin peptides. Characterization of receptors. Hypertension 19 (Suppl II):II49-II-55]. AII is able to stimulate the release of prostanoids in other cells types and in intact blood vessels but not human or porcine endothelial cells. This effect on endothelial cells was through a receptor distinct from AT1 and AT2.

In rat glomerulus preparations, AII inhibited the formation of cAMP in response to histamine, serotonin and parathyroid hormone through the AT1 receptor [Edwards, R M and E J Stack. 1993. Angiotensin II inhibits glomerular adenylate cyclase via the angiotensin II receptor subtype 1 (AT1). J Pharmacol Exper Ther 266:506–510]. AII(1–7) did not have this effect.

In porcine vascular smooth muscle cells and human astrocytes, AII and AI(1–7) increases prostaglandin release; only angiotensin II increases the release of intracellular Ca2+ [Jaiswal et al. 1993. Differential regulation by angiotensin peptides in porcine aortic smooth muscle cells: subtypes of angiotensin receptors involved. J Pharmacol and Exp Therapeutic 265:664–673; Jaiswal et al. 1991. Subtype 2 angiotensin receptors mediate prostaglandin synthesis in human astrocytes. Hypertension 17:1115–1120].

AII(1–7) dilates porcine coronary artery rings, perhaps through nitric oxide [Porsti et al. 1994. Release of nitric oxide by angiotensin-(1–7) from porcine coronary endothelium: implications for a novel angiotensin receptor. Br. J Pharmacol 111:652–654]. This was not observed with AII, AIII or AII(3–8). This effect was not attenuated by antagonists of AT1 or AT2 receptors.

AII causes depolarization of rat isolated nodose ganglion; AII(1–7) does not [Widdop et al. 1992. Electrophysiological responses of angiotensin peptides on the rat isolated nodose ganglion. Clin and Exper Hyper-Theory and Practice A14:597–613]. Indeed, AII(1–7) may have novel actions on brain function [Schiavone et al. 1990. Angiotensin-[1–7]: Evidence for novel actions in the brain. J Cardiovascular Pharmacol 16(Suppl 4):S19–S24].

There are activities that AII(1–7) shares with AII, such as release of vasopressin and modulation of phospholipase A2 activity in proximal tubule cells [Andreatta-Van Leyen, S et al. 1993. Modulation of phospholipase A2 activity and sodium transport by angiotensin-(1–7). Kidney International 44:932–6; Moriguchi, A et al. 1994. Differential regulation of central vasopressin in transgenic rats harboring the mouse Ren-2 gene. Am J Physiol 267:R786–R791; Ferrario et al. 1991. Angiotensin-(1-7): A new hormone of the angiotensin system. Hypertension 19[suppl III]:III-126-III-133]. These activities, however, are likely not involved in wound repair.

The effects of other fragments of AII have been studied in very few instances. Most neurons in the paraventricular nucleus are excited by Ang(1–7), AII and AIII, but AII(1–7) is weaker in this effect; in many neurons, AII(2–7) was inactive [Ambuhl et al. 1992. Effects of angiotensin analogues and angiotensin receptor antagonists on paraventricular neurones. Regulatory Peptides 38:111–120]. AII injected in the lateral cerebral ventricle increased the motility, stereotypy and learning of conditioned avoidance responses; AII(1–6) and AII(2–6) were not active in these psychotropic activities [Holy, Z et al. 1993. Psychotropic effects of angiotensin II N-terminal fragments: Asp—Arg—Val—Tyr—Ile—His (SEQ ID NO: 8) and Arg—Val—Tyr—Ile—His (residues 2–6 of SEQ ID NO: 8) in rats. Polish J Pharmacol 45:31–41].

AII(4–8), AII(5–8) and AII(1–4) showed only a slight effect on water intake when injected into the anterior diencephalon in the rat, and AII(1–7) was completely inactive [Fitzsimmons, J T. 1971. The effect on drinking of peptide precursors and of shorter chain peptide fragments of angiotensin II injected into the rat's diencephalon. J Physiol 214:295–303]. Intracerebroventricular infusion of AII fragments [AII(4–8) and AII(5–8)] in the rat produced a minimal effect on blood pressure even when given at concentrations 1000× higher than that of AII that increased blood pressure [Wright et al. 1989. Structure-function analyses of brain angiotensin control of pressor action in rats. Am J Physiol 257:R1551–R1557]. In both of these studies, the fragments were injected directly into the brain; this is highly artificial and does not allow for systemic metabolism.

According to the method of the invention, an active fragment or analog thereof in accordance with the present invention is applied to wound tissue in amounts sufficient to increase the healing rate of tissue. These compounds can significantly accelerate the rate of healing at nanomolar levels in vivo. For any given active agent, the optimum concentration for a given formulation may readily be determined empirically. In general, an amount of active agent suitable for use in accordance with the present invention ranges from about 0.0001 $\mu$g to about 10 mg per kilogram body weight.

The compounds of the invention may be applied in a variety of solutions. Suitable solutions for use in accordance with the present invention are sterile, dissolve sufficient amounts of the peptide, and are not harmful to wound tissue. In this regard, the compounds of the present invention are very stable but are hydrolyzed by strong acids and bases. The compounds of the present invention are soluble in organic solvents and in aqueous solutions at pH 5–8.

Any type of application means may be employed which permits the influx of the active agents into the tissue over a period of time. For example, an aqueous solution could be applied to the wound tissue through a gauze bandage or strip, or such a solution could be formulated so that a timed perfusion may be obtained (using, e.g., liposomes, ointments, micelles, etc). Methods for the production of these formulations with the compounds of the present invention are apparent to those of ordinary skill in the art. The particular concentration of active agent employed is not critical, as the tissue-repairing effect is present even when the compounds are present in nanomolar quantities.

Preferably, a matrical or micellar solution is employed with the active agent present in a concentration of at least 30 micrograms per milliliter. A particular matrical solution which has been used to advantage in the described examples is a semi-solid polyethylene glycol polymer sold under the trademark Hydron by Hydro Med Sciences, New Brunswick, N.J. Another preferred solution is a micellar solution sold under the trade name Pluronics F108 by BASF, Ludwigshafen, Germany. Under room temperature conditions, this solution is a liquid, but when applied to warm tissue the solution forms a gel which permits the infusion of active agent into the wound tissue for a period of several days. Other preferred formulations include carboxymethyl cellulose preparations (as used in the example herein), crystalloid preparations (e.g., saline, Ringer's lactate solution, phosphate-buffered saline, etc.), viscoelastics, polyethylene glycols, polypropylene glycols and wound dressings (e.g., bandages, etc.).

The healing effects of the compounds of the present invention may be provided in a variety of instances. The solution may be applied topically to surface wound tissue in the treatment of ulcers, lesions, injuries, diabetic ulcers, burns, trauma, stasis ulcers, periodontal conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active agent prior to closing the surgical site in order to accelerate internal capillary perfusion and healing. In addition, the rate of localized healing may be increased by the subdermal administration of active agent by injection or otherwise.

The invention may be better understood with reference to the accompanying example, which is intended for purposes of illustration only and should not be construed as in any sense limiting the scope of the invention as defined in the claims appended hereto.

EXAMPLE 1

Male Sprague Dawley rats, 12 weeks old, were obtained from Simonsen Laboratories, Gilroy, Calif. On the day of surgery, the rats received intramuscular ketamine/rompum anesthesia prior to preparation for surgery. The rats were shaved and scrubbed with betadine. Four 2×2 cm full thickness dermal wounds were created on the dorsal surface of the rat. Following excision of the skin, the size of the wound was outlined on a glass slide and the medicament was administered in 100 $\mu$l Hydron solution comprising 10% Hydron, 1% polyethylene glycol (MW 400) and 60% ethanol. The test materials were administered in a randomized fashion; angiotensin III was evaluated at 3 and 10 $\mu$g/wound. Controls were treated with vehicle only.

After administration of the materials, the rats were bandaged and allowed to recover from anesthesia. At days 2, 5, 6, 8 and 10, the area of the skin wounds were measured under methoxyflurane anesthesia (commercially available as Metofane from Pittman-Moore, Mundelein, Ill.). The area of the wound was determined by: (1) tracing the wound shape onto graph paper (1×1 mm squares); (2) cutting out the shape; (3) weighing the paper and comparing the weight with a 2×2 cm paper cutout; and (4) counting the number of squares.

As illustrated in FIG. 1, wound closure was substantially accelerated relative to the control animals when the test animals were treated with angiotensin III, at both the 3 $\mu$g and the 10 μg dosages. FIG. 1 illustrates the percent increase in wound closure relative to a vehicle-treated control.

EXAMPLE 2

Female Sprague Dawley rats, 12 weeks old, were obtained from Simonsen Laboratories, Gilroy, Calif. and prepared for surgery as in Example 1. Two 1.5×1.5 cm full thickness dermal wounds were created on the dorsal surface of the rat. Following excision of the skin, the size of the wound was outlined on a glass slide and the medicament was administered in 100 μl Hydron solution comprising 10% Hydron, 1% polyethylene glycol (MW 400) and 60% ethanol. The test materials were administered in a randomized fashion; all materials were tested at 10 μg/wound. Controls were treated with vehicle only. After administration of the materials, the rats were bandaged and allowed to recover from anesthesia. At days 2–3, 5, 7–8 and 9–10, the area of the skin wounds were measured (for analogs 1A and 2–8) under methoxyflurane anesthesia (commercially available as Metofane from Pittman-Moore, Mundelein, Ill.). The area of the wound was determined by: (1) tracing the wound shape onto graph paper (1×1 mm squares); (2) cutting out the shape; (3) weighing the paper and comparing the weight with a 1.5×1.5 cm paper cutout; and (4) counting the number of squares. In addition, on days 2–3, 5 and 8, the area of granulation tissue was similarly determined (for analogs 1A, 1B and 2–7). The analogs employed were the following:

| | |
|---|---|
| Analog 1A | Ile$^7$-angiotensin III |
| Analog 1B | Val$^4$-angiotensin III |
| Analog 2 | Lys$^1$-angiotensin III |
| Analog 3 | Ala$^2$-angiotensin III |
| Analog 4 | Thr$^3$-angiotensin III |
| Analog 5 | Leu$^4$-angiotensin III |
| Analog 6 | Arg$^5$-angiotensin III |
| Analog 7 | Ala$^6$-angiotensin III |
| Analog 8 | Tyr$^7$-angiotensin III |

Figure 2:
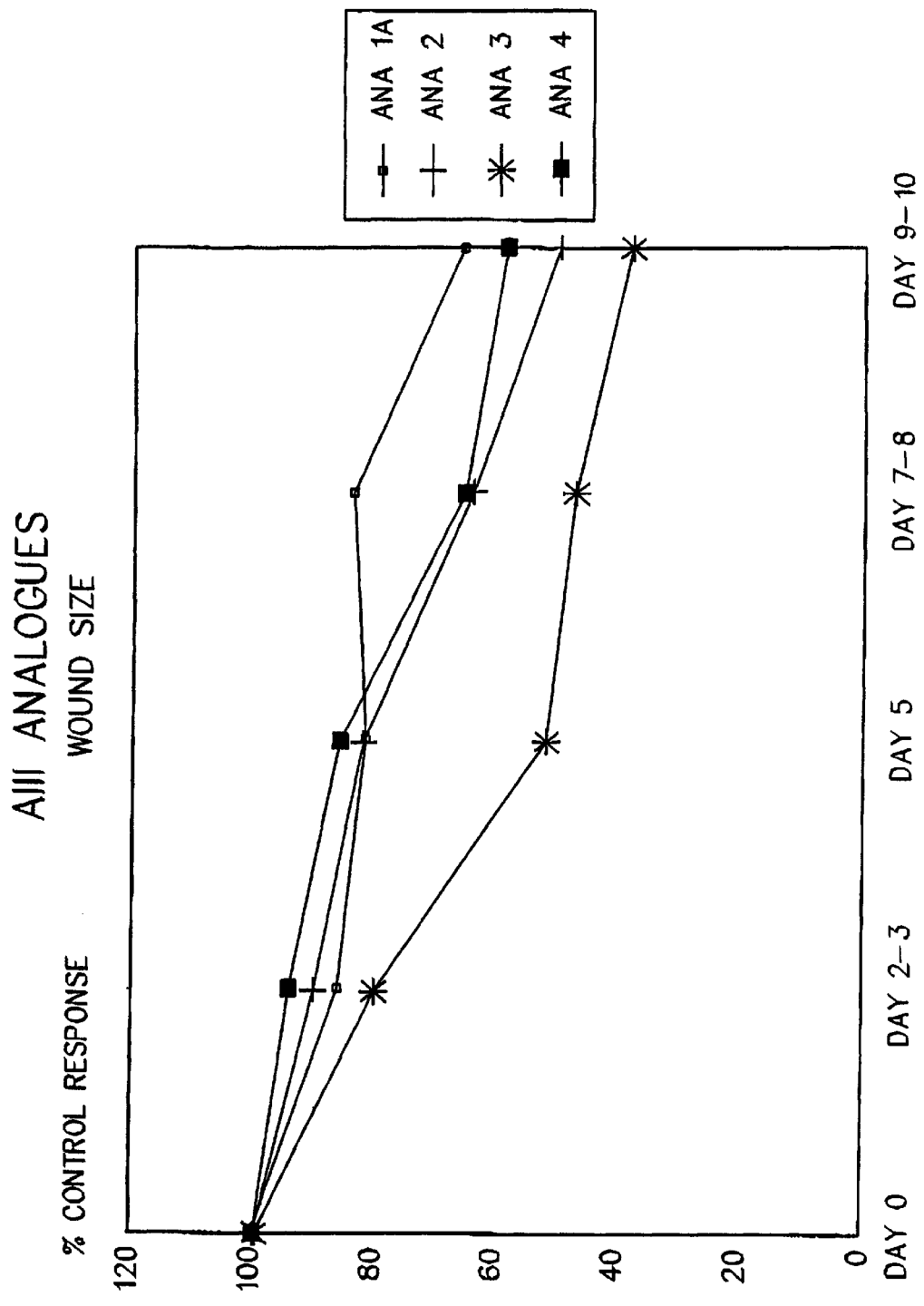
FIG. 2 illustrates the percent of control response in wound closure relative to a vehicle-treated control using various AIII analogs.
Figure 3:
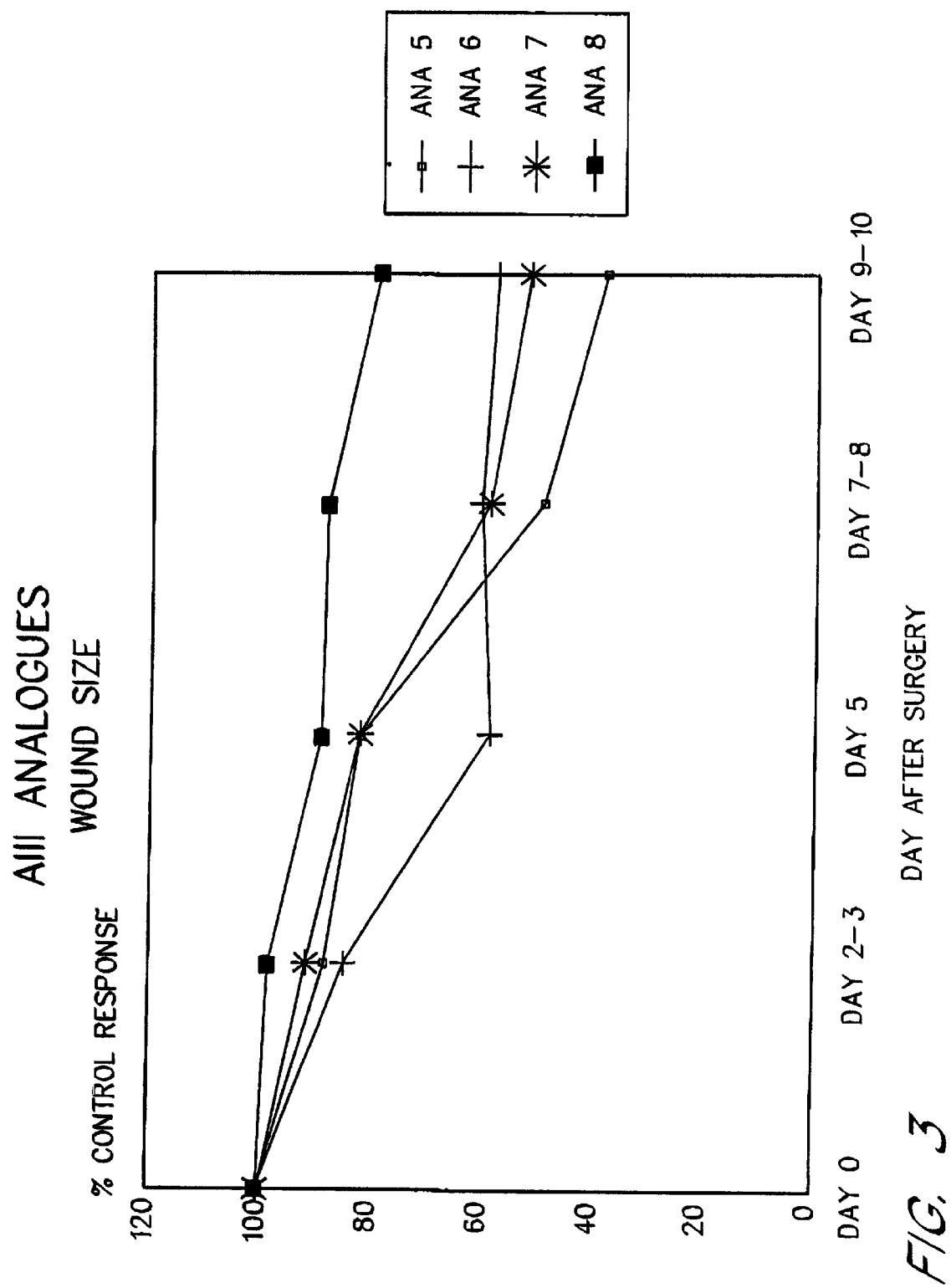
FIG. 3 illustrates the percent of control response in wound closure relative to a vehicle-treated control using various AIII analogs.
Figure 4:
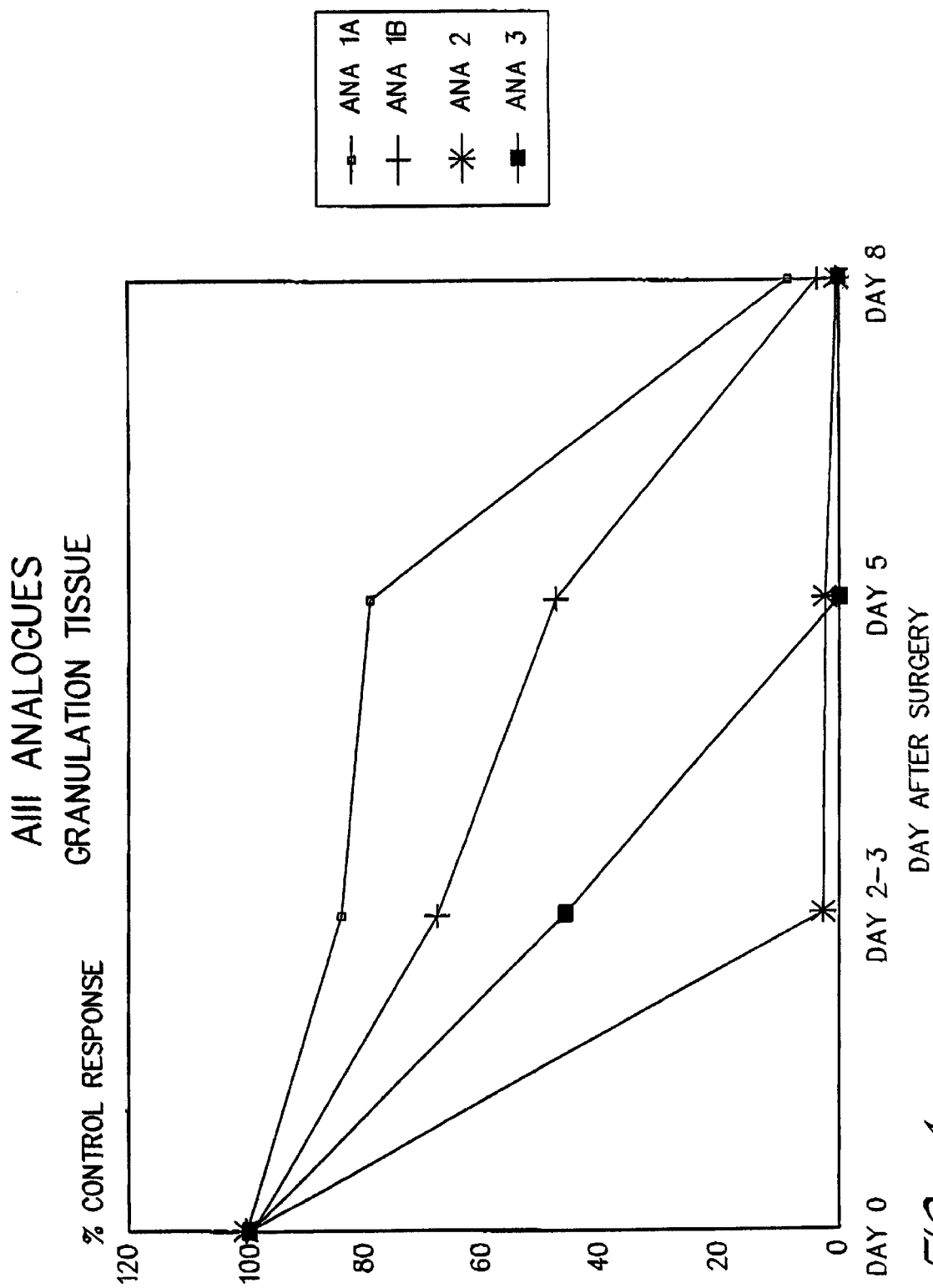
FIG. 4 illustrates the percent of control response in formation of granulation tissue using various AIII analogs.
Figure 5:
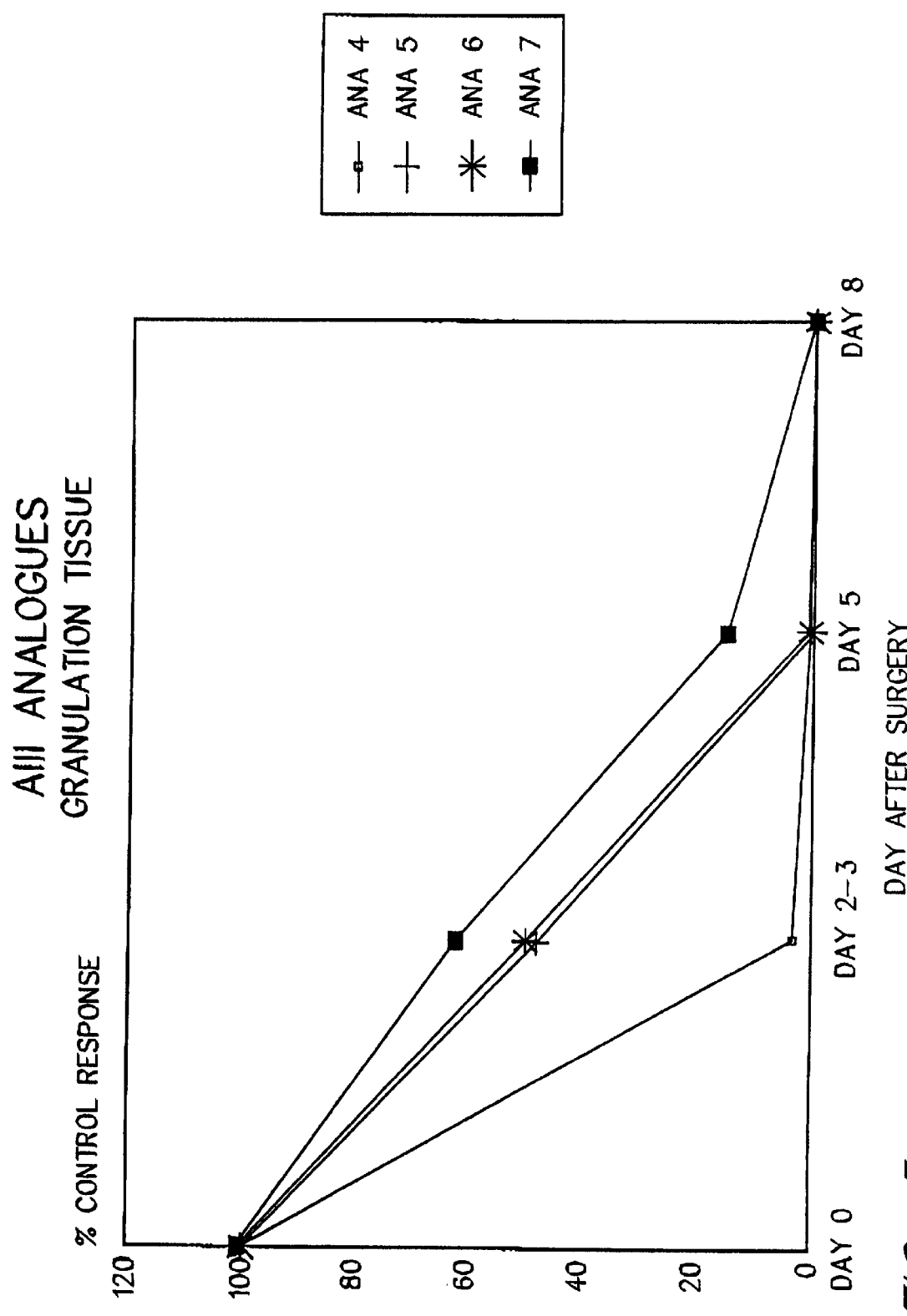
FIG. 5 illustrates the percent of control response in formation of granulation tissue using various AIII analogs.

As illustrated in FIGS. 2–5 attached hereto, wound closure was substantially accelerated relative to the control wounds when the test wounds were treated with Analogs 1–8 in accordance with general formula I. FIGS. 2 and 3 illustrate the percent of control response in wound closure relative to a vehicle-treated control; in every case, administration of one of the analogs accelerated the closure of the wound after surgery. FIGS. 4 and 5 illustrate the percent of control response in formation of granulation tissue; again, in every case administration of one of the analogs accelerated the formation of granulation tissue compared to administration of vehicle alone. Therefore, these analogs clearly are effective in promoting wound healing.

EXAMPLE 3

Female Sprague Dawley rats, 175–200 g, were obtained from Simonsen Laboratories, Gilroy, Calif. On the day of surgery, the rats received intramuscular ketamine/rompum anesthesia prior to preparation for surgery. The rats were shaved and scrubbed with betadine. Two 1.5×1.5 cm full thickness dermal wounds were created on the dorsal surface of the rat. Following excision of the skin, the size of the wound was outlined on a glass slide and the medicament was administered in 100 μl 10% low viscosity carboxymethyl cellulose (Sigma). The test materials were administered in a randomized fashion; all materials were tested at 100 μg/wound. Controls were treated with vehicle only. After administration of the materials, the rats were bandaged and allowed to recover from anesthesia. On days 1–4 after surgery, the rats were treated with an additional 100 μg of peptide formulation. At days 2, 4, 7 and 9, the area of the skin wounds were measured under methoxyflurane anesthesia (commercially available as Metofane from Pittman-Moore, Mundelein, Ill.). The area of the wound was determined by: (1) tracing the wound shape onto graph paper (1×1 mm squares); (2) cutting out the shape; (3) weighing the paper and comparing the weight with a 1.5×1.5 cm paper cutout; and (4) counting the number of squares. In addition, on days 2, 4 and 7, the area of granulation tissue was similarly determined.

Figure 6:
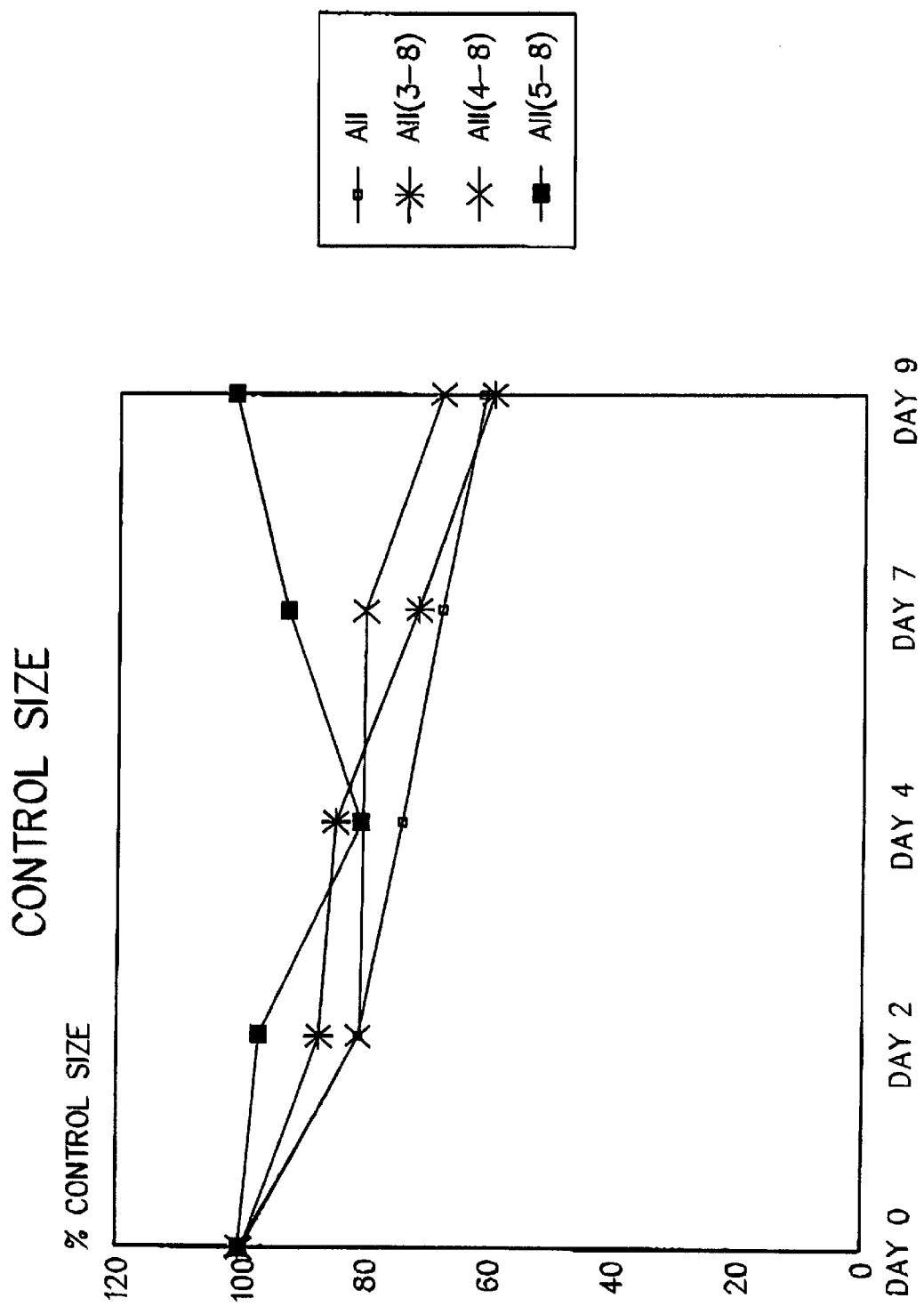
FIG. 6 illustrates the percent of control response in wound closure relative to a vehicle-treated control using various fragments of AII.
Figure 7:
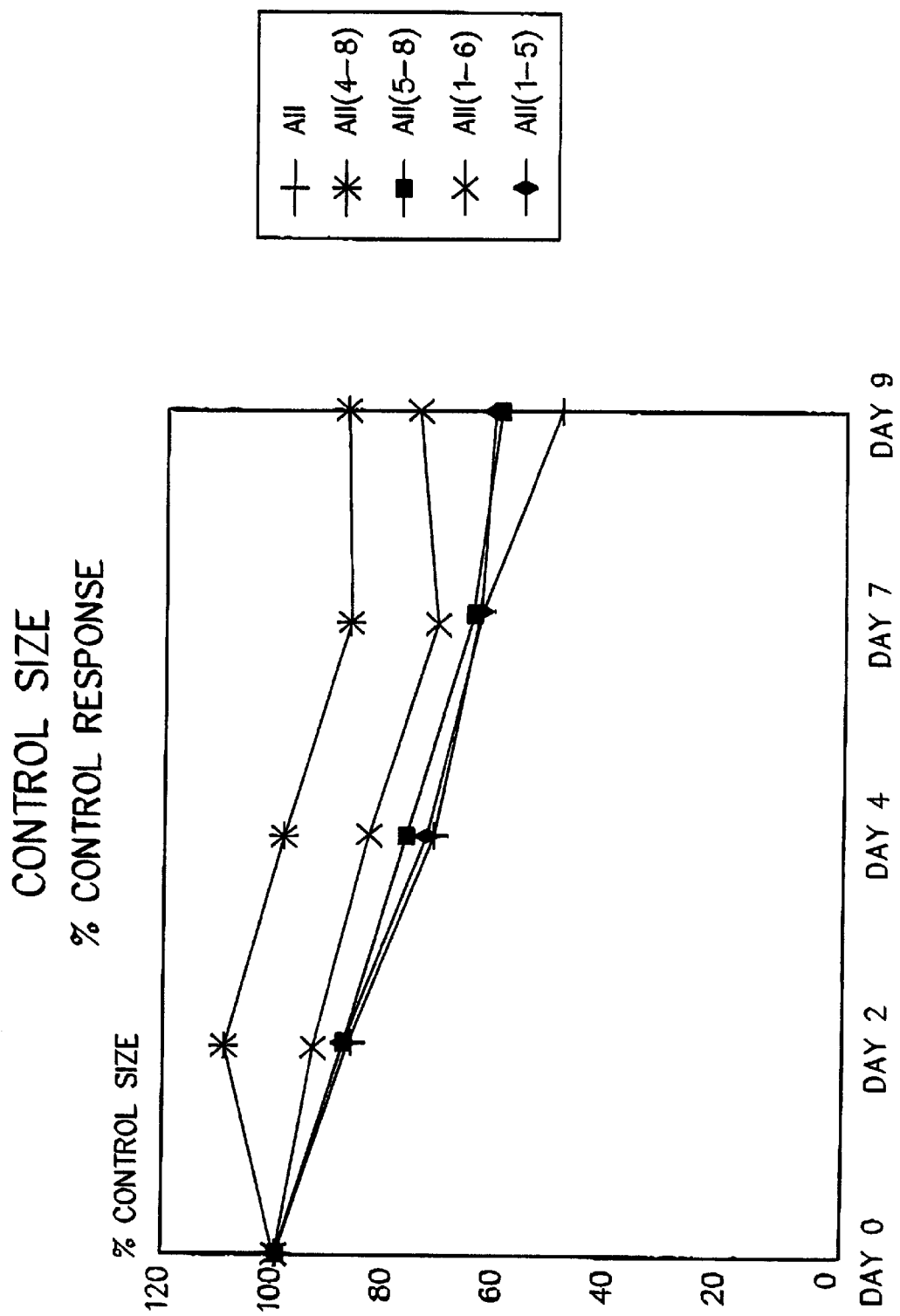
FIG. 7 illustrates the percent of control response in wound closure relative to a vehicle-treated control using various fragments of AII.
Figure 8:
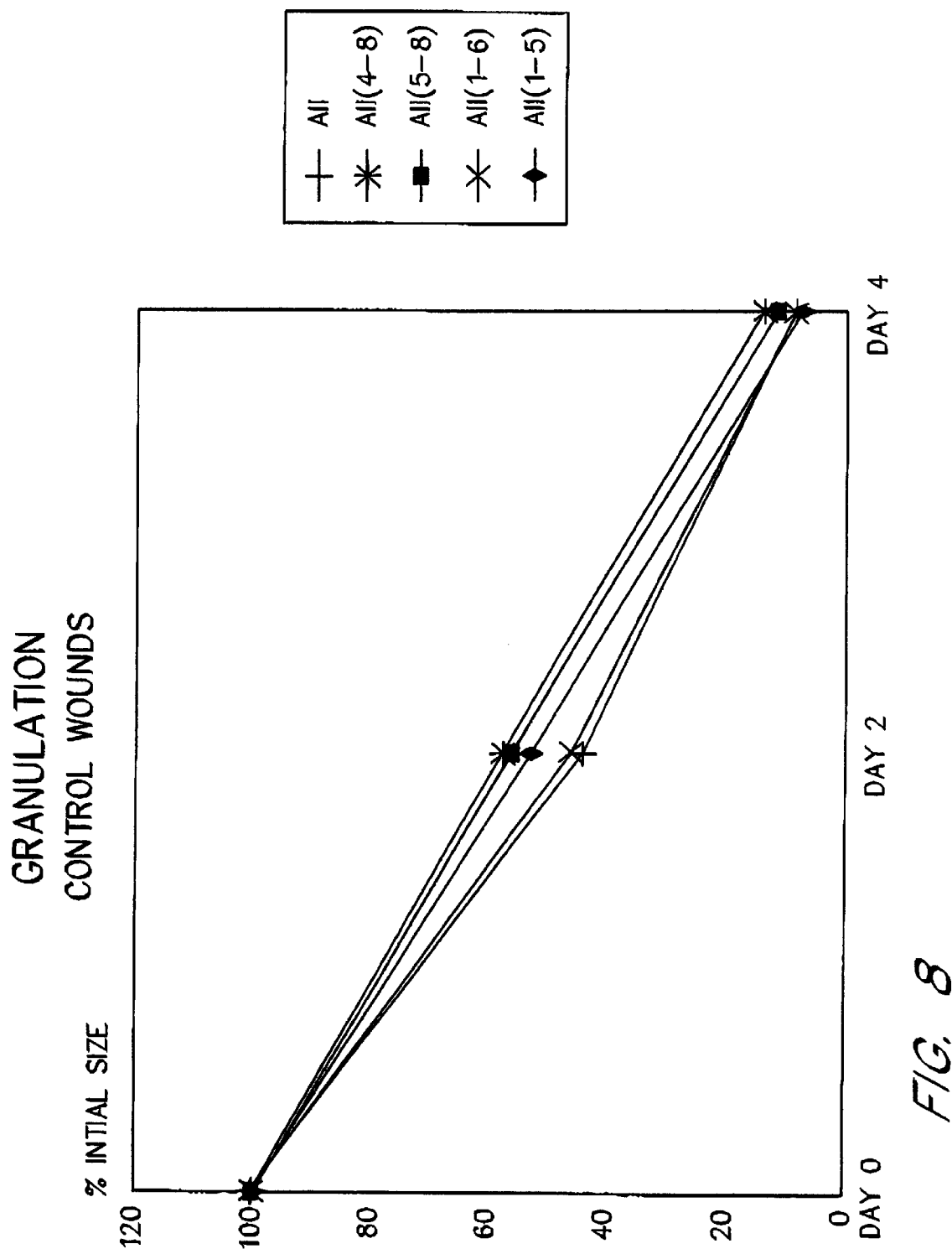
FIG. 8 illustrates the percent of control response in formation of granulation tissue using various fragments of AII.
Figure 9:
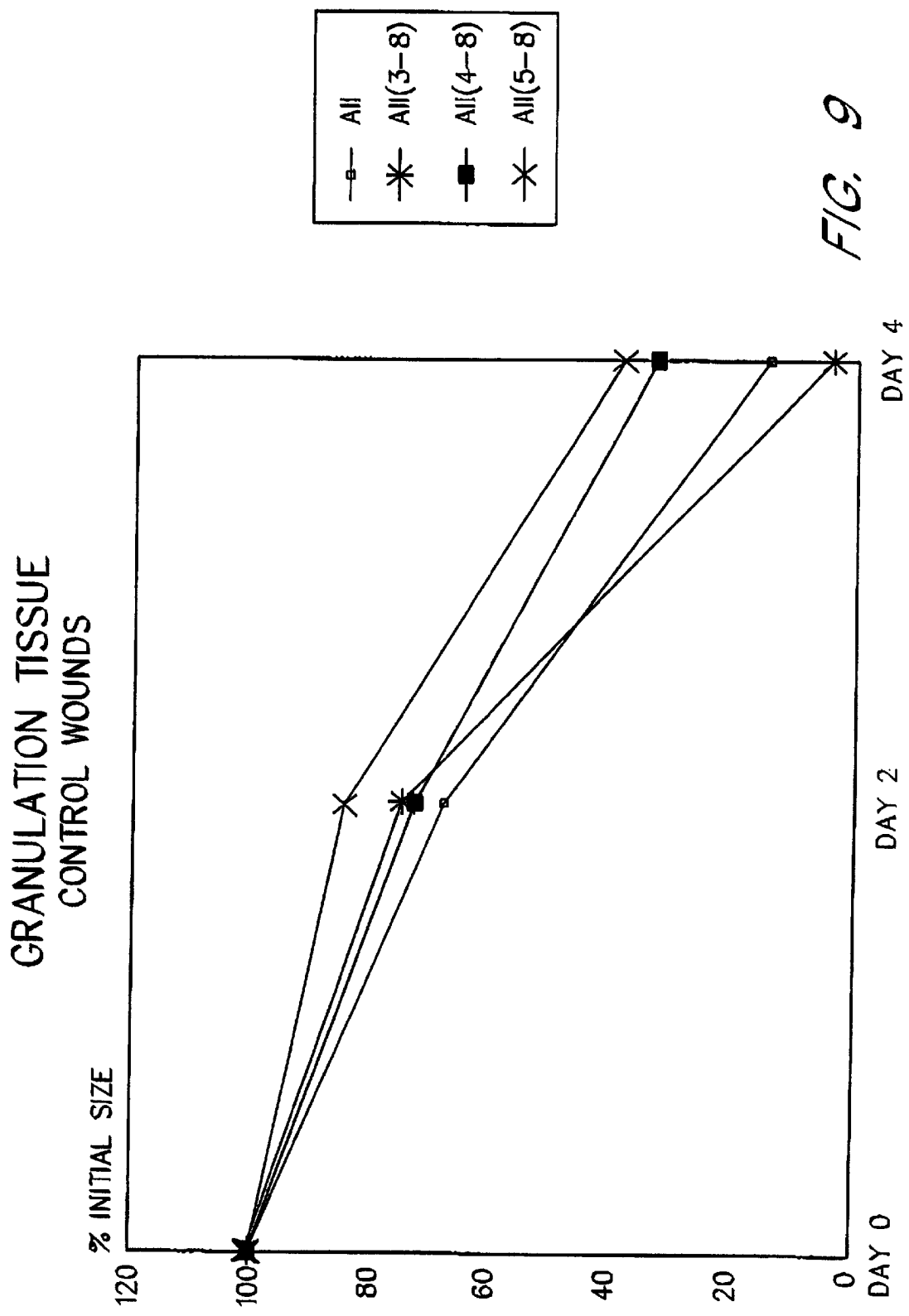
FIG. 9 illustrates the percent of control response in formation of granulation tissue using various fragments of AII.
Figure 10:
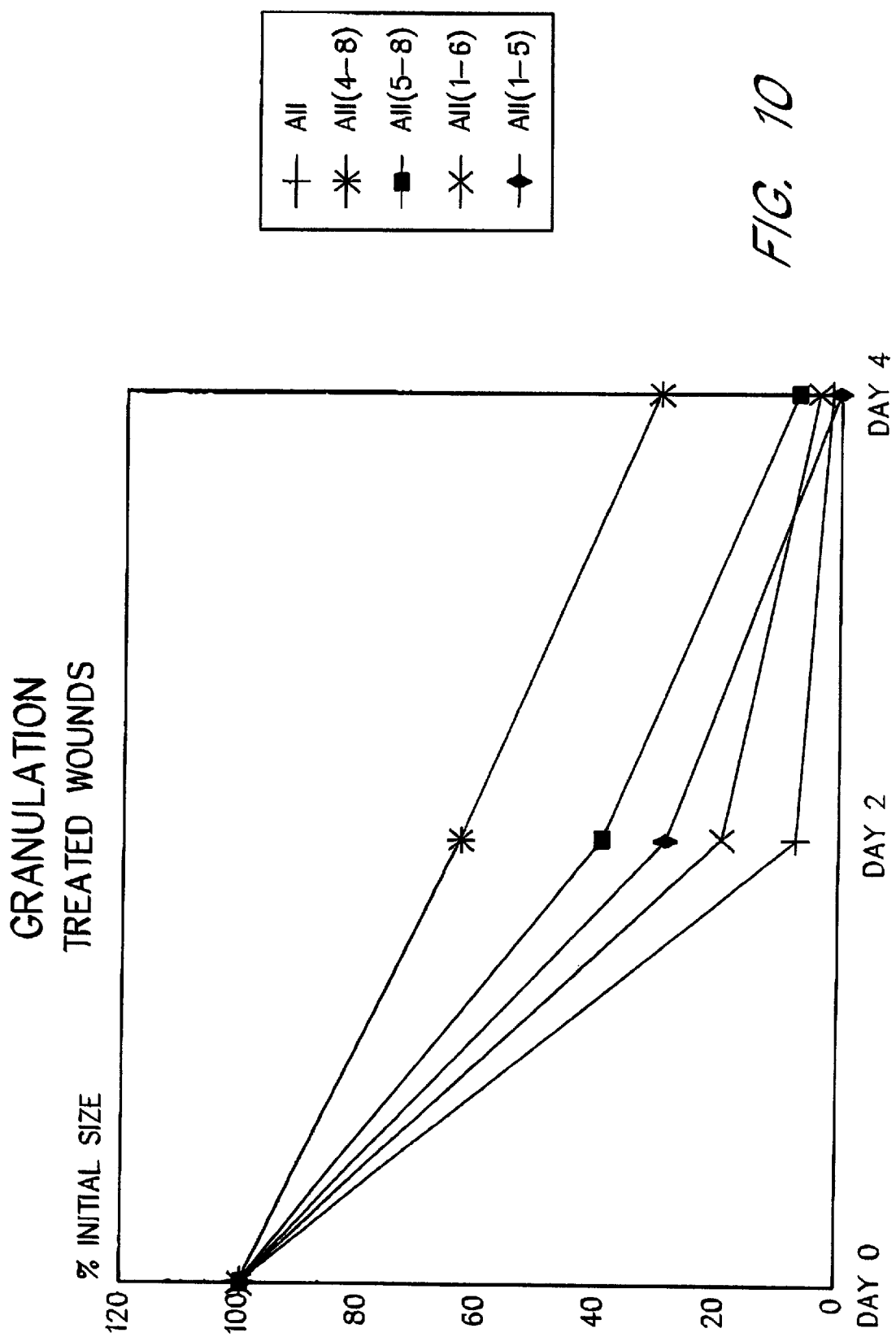
FIG. 10 illustrates the percent of control response in formation of granulation tissue using various fragments of AII.
Figure 11:
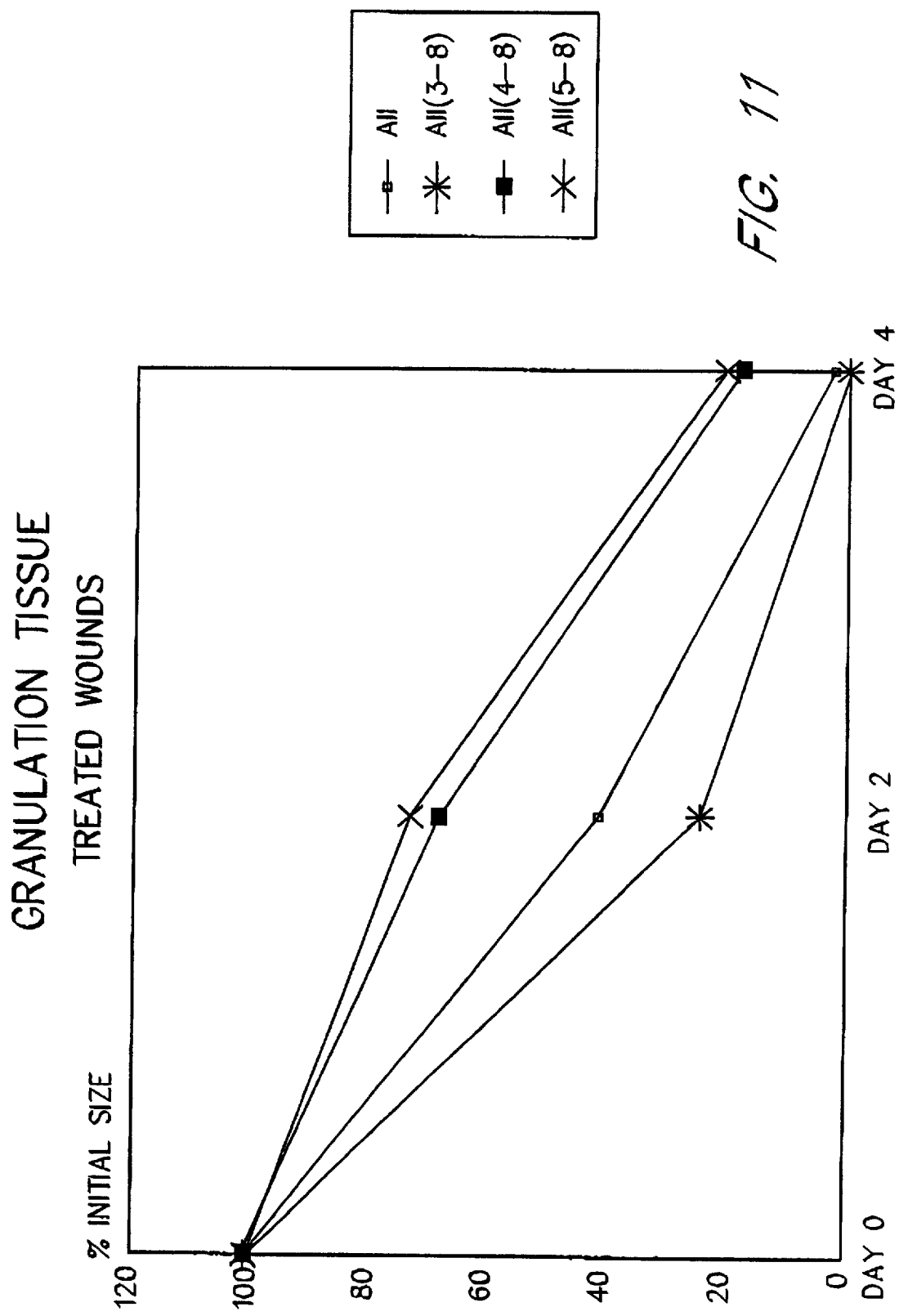
FIG. 11 illustrates the percent of control response in formation of granulation tissue using various fragments of AII.
Figure 12:
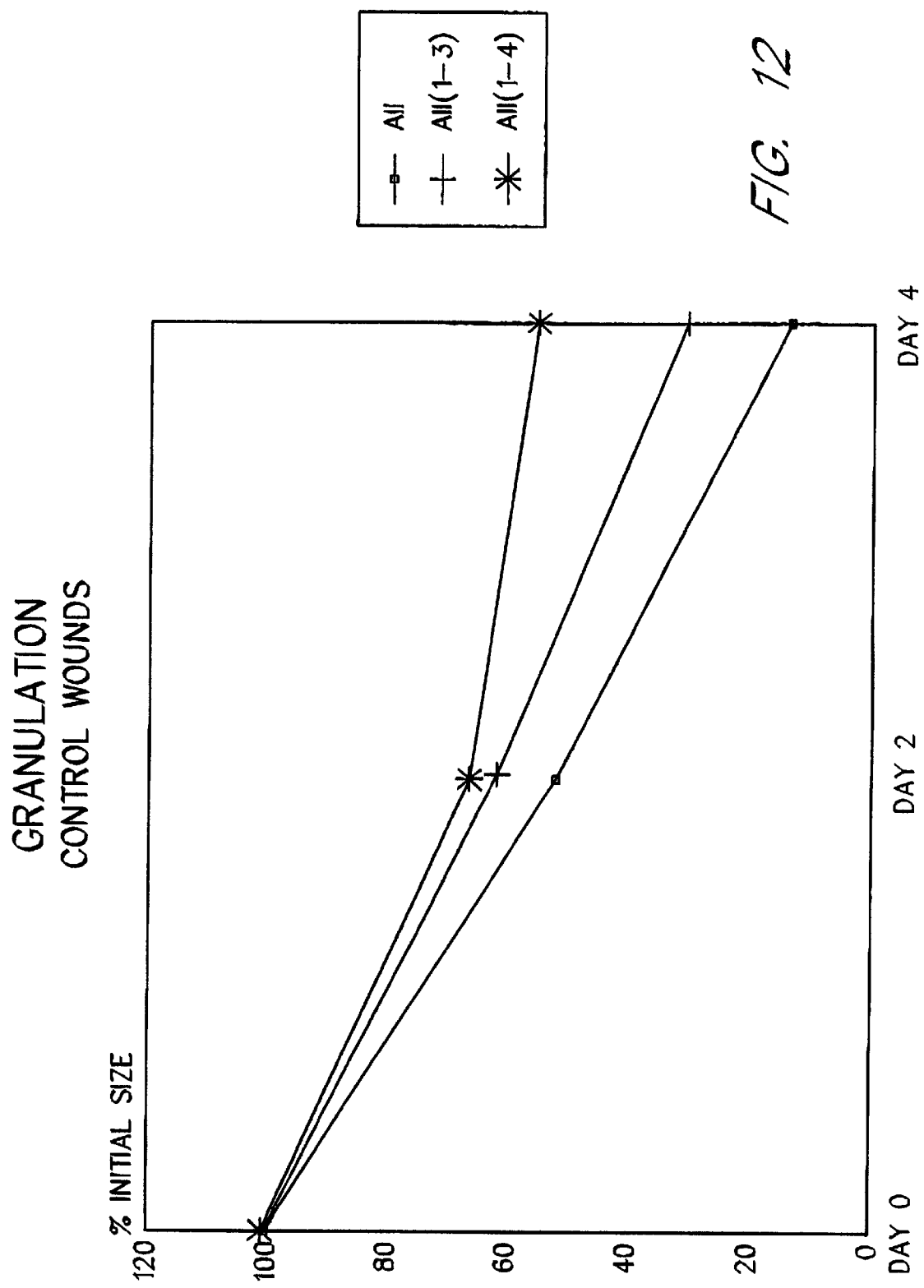
FIG. 12 illustrates the percent of control response in formation of granulation tissue using various AIII analogs.
Figure 13:
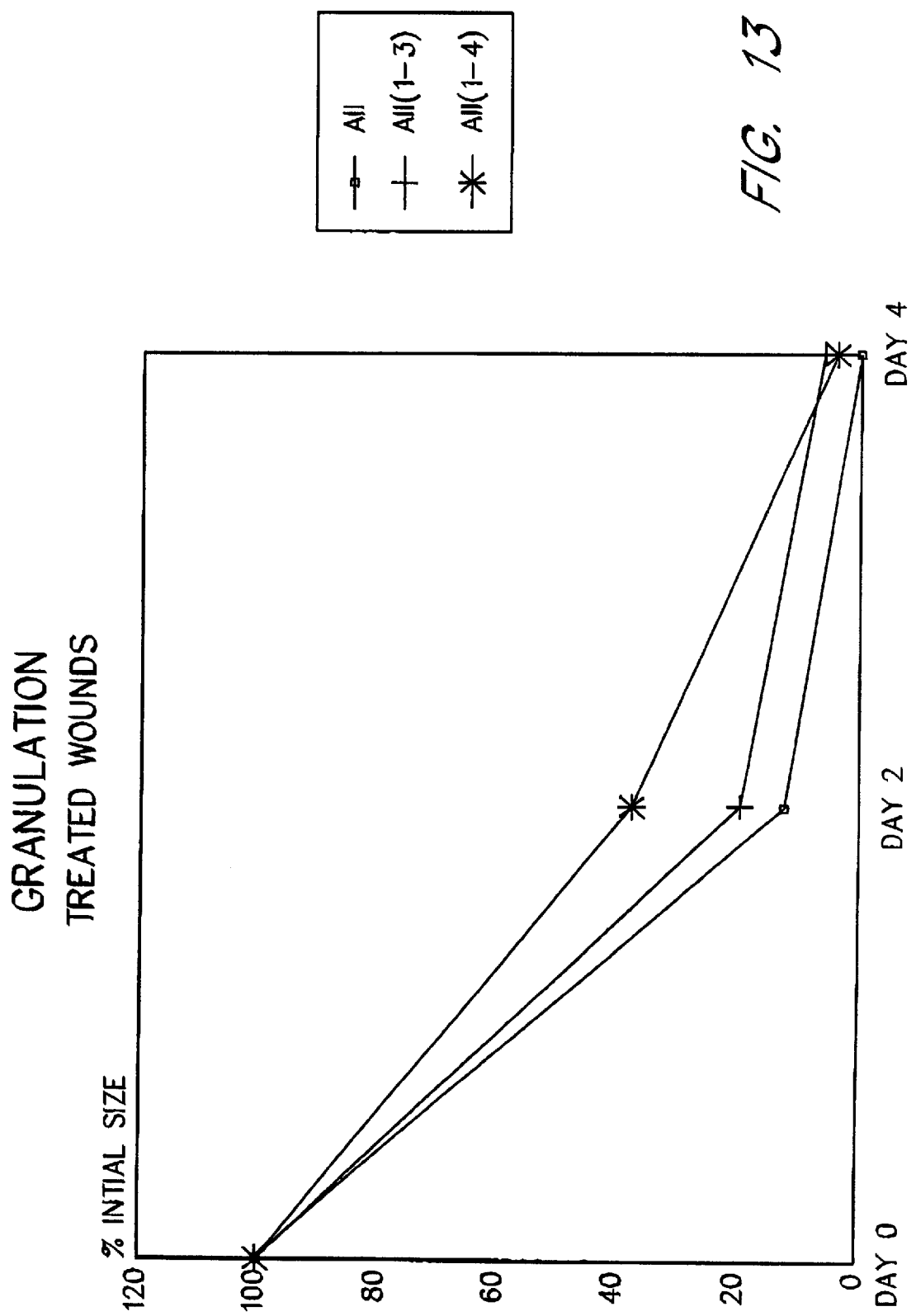
FIG. 13 illustrates the percent of control response in formation of granulation tissue using various AIII analogs.
Figure 14:
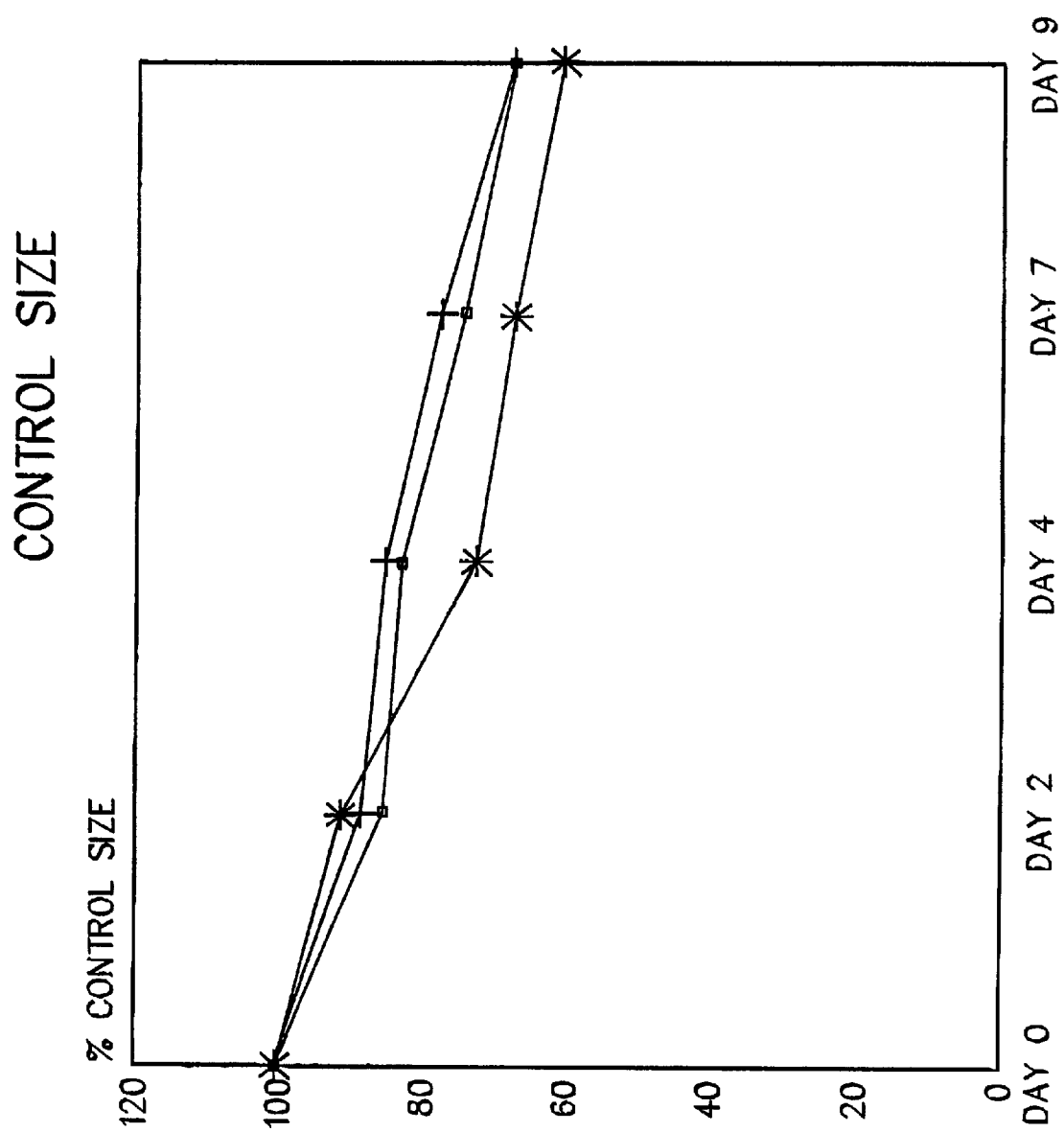
FIG. 14 illustrates the percent of control response in wound closure relative to a vehicle-treated control using various fragments of AII.

As illustrated in FIGS. 6–11, wound closure was substantially accelerated relative to the control animals when the test animals were treated with all fragments except AII(6–8) and AII(4–8). FIGS. 6 and 7 illustrate the percent of control response in wound closure relative to a vehicle-treated control using fragments of AII as herein defined. FIGS. 8–11 illustrate the percent of control response in formation of granulation tissue; FIGS. 8 and 9 reflect data from control wounds to which FIGS. 10 and 11, respectively, should be compared.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

---

What is claimed is:

1. A method of accelerating wound healing, comprising applying to a wound an effective amount to accelerate wound healing of at least one peptide other than Angiotensin II, said peptide consisting of at least three contiguous amino acids and having a sequence corresponding to a subsequence of groups $R^1$—$R^8$ in general formula I:

$R^1$—$R^2$—$R^3$—$R^4$—$R^5$—$R^6$—$R^7$—$R^8$ (SEQ ID NO:15), wherein $R^1$ is selected from the group consisting of Asp, Glu, Asn, Acpc, Ala, $Me^2Gly$, Pro, Bet, Glu ($NH_2$), Gly, Asp ($NH_2$) and Suc;

$R^2$ is selected from the group consisting of Arg, Lys, Ala, Orn, Ser(Ac), Sar, D-Arg and D-Lys;

$R^3$ is selected from the group consisting of Val, Ala, Leu, Ile, Gly, Pro, Aib, Acpc and Tyr;

$R^4$ is selected from the group consisting of Tyr, Thr, Ser and azaTyr;

$R^5$ is selected from the group consisting of Ile, Ala, Leu, Val and Gly;

$R^6$ is His or Arg;

$R^7$ is Pro or Ala; and $R^8$ is selected from the group consisting of Phe, Phe(Br), Ile and Tyr, excluding sequences wherein $R^4$ is an amino terminal Tyr group of the peptide.

2. A method according to claim 1, wherein the peptide is administered in matrical or micellar solution.

3. A method according to claim 1, wherein the peptide is administered in an amount of at least 0.1 ng per kg body weight in a suitable carrier or diluent.

4. A method according to claim 3, wherein the carrier or diluent is selected from the group consisting of carboxymethyl cellulose preparations, crystalloid preparations, viscoelastics, polyethylene glycols and polypropylene glycols.

5. A method according to claim 1, wherein the peptide is administered in conjunction with a wound dressing.

6. A method according to claim 1, wherein the peptide has a sequence consisting of $R^1$—$R^2$—$R^3$ in general formula I.

7. A method according to claim 6, wherein the peptide has a sequence consisting of Asp—Arg—Val (SEQ ID NO: 11).

8. A method according to claim 1, wherein the peptide has a sequence consisting of $R^1$—$R^2$—$R^3$—$R^4$ in general formula I.

9. A method according to claim 8, wherein the peptide has a sequence consisting of Asp—Arg—Val—Tyr (SEQ ID NO: 10).

10. A method according to claim 1, wherein the peptide has a sequence consisting of $R^1$—$R^2$—$R^3$—$R^4$—$R^5$ in general formula I.

11. A method according to claim 10, wherein the peptide has a sequence consisting of Asp—Arg—Val—Tyr—Ile (SEQ ID NO:9).

12. A method according to claim 1, wherein the peptide has a sequence consisting of $R^1$—$R^2$—$R^3$—$R^4$—$R^5$—$R^6$ in general formula I.

13. A method according to claim 12, wherein the peptide has a sequence consisting of Asp—Arg—Val—Tyr—Ile—His (SEQ ID NO:8).

14. A method according to claim 1, wherein the peptide has a sequence consisting of $R^3$—$R^4$—$R^5$—$R^6$—$R^7$ in general formula I.

15. A method according to claim 14, wherein the peptide has a sequence consisting of Val—Tyr—Ile—His—Pro (SEQ ID NO:6).

16. A method according to claim 1, wherein the peptide has a sequence consisting of $R^2$—$R^3$—$R^4$—$R^5$—$R^6$—$R^7$ in general formula I.

17. A method according to claim 16, wherein the peptide has a sequence consisting of Arg—Val—Tyr—Ile—His—Pro (SEQ ID NO:5).

18. A method according to claim 1, wherein the peptide has a sequence consisting of $R^3$—$R^4$—$R^5$—$R^6$—$R^7$—$R^8$ in general formula I.

19. A method according to claim 18, wherein the peptide has a sequence consisting of Val—Tyr—Ile—His—Pro—Phe (SEQ ID NO:3).

20. A method according to claim 1, wherein the peptide has a sequence consisting of $R^5$—$R^6$—$R^7$—$R^8$ in general formula I.

21. A method according to claim 20, wherein the peptide has a sequence consisting of Ile—His—Pro—Phe (SEQ ID NO:7).

* * * * *